United States Patent [19]
Grosse et al.

[11] 4,069,082
[45] Jan. 17, 1978

[54] PROCESS FOR THE TRANSFORMATION OF A COMMINUTED SWELLABLE CELLULOSE ETHER INTO AN EASILY WORKABLE MATERIAL

[75] Inventors: Ludwig Grosse, Taunusstein; Hans-Werner Dörr, Wiesbaden, both of Germany

[73] Assignee: Hoechst Aktiengesellschaft, Germany

[21] Appl. No.: 747,958

[22] Filed: Dec. 6, 1976

[30] Foreign Application Priority Data

Dec. 4, 1975 Germany .............................. 2554558

[51] Int. Cl.$^2$ ........................... B05D 1/28; B05D 7/00
[52] U.S. Cl. ..................................... 156/281; 106/187; 106/188; 106/189; 106/190; 106/197 R; 427/394
[58] Field of Search ............... 162/157 R, 157 C, 102, 162/177; 106/197 R, 197 C, 187, 188, 189, 190; 427/394–396, 415; 128/274, 285, 290; 156/281, 279

[56] References Cited

U.S. PATENT DOCUMENTS

| 2,045,052 | 6/1936 | Rafton ................................. 162/177 |
| 2,639,239 | 5/1953 | Elliott ............................. 106/197 R |
| 2,889,056 | 6/1959 | Freeder ............................. 118/602 X |
| 3,493,407 | 2/1970 | Greminger, Jr. et al. ... 106/197 R X |
| 3,589,364 | 6/1971 | Dean et al. ....................... 162/146 X |
| 3,661,154 | 5/1972 | Torr ..................................... 128/284 |
| 3,674,621 | 7/1972 | Miyamoto et al. ............. 162/157 R |
| 3,723,413 | 3/1973 | Chatterjee et al. ............. 128/285 X |
| 3,899,439 | 8/1975 | Mahlman ..................... 106/197 R X |
| 3,901,236 | 8/1975 | Assarsson et al. ............. 128/290 R |
| 3,953,282 | 4/1976 | Tabara et al. ..................... 162/102 |

*Primary Examiner*—Morris Kaplan
*Attorney, Agent, or Firm*—James E. Bryan

[57] ABSTRACT

This invention relates to an improvement in the process for the transformation of comminuted cellulose ether, which has been rendered at least largely water-insoluble by modification, but which is still highly swellable with water, into an easily workable material, in which process the modified cellulose ether is attached to a hydrophilic support web, the improvement comprising dispersing the modified cellulose ether in a solution of unmodified cellulose ether in an organic solvent, coating the support on at least one of its surfaces with the dispersion, and then drying.

8 Claims, No Drawings

PROCESS FOR THE TRANSFORMATION OF A COMMINUTED SWELLABLE CELLULOSE ETHER INTO AN EASILY WORKABLE MATERIAL

The present invention relates to a process for the transformation of a comminuted and modified cellulose ether swellable with water, into a material that may be easily further processed and thus may be used without difficulty in the production of hygienic pads, napkins, bandages, tampons, wrapping papers, insulating material, household papers and similar articles.

For the manufacture of such products, tissues or fleeces are used that can absorb aqueous liquids, in particular physiological body fluids such as blood or urine. In copending application Ser. No. 709,269, filed July 28, 1976, a coated web composed of a hydrophilic material is disclosed, at least one surface of which is provided with a comminuted modified cellulose ether which is used for improving the absorption capacity of such products. In the same application, a process for the production of these coated webs is disclosed, i.e., a process for the transformation of comminuted cellulose ether, which has been rendered at least largely water-insoluble by modification but has remained highly swellable with water, into an easily usable material. In this process, the comminuted and modified cellulose ether is attached to a hydrophilic web support, at least one surface of the web is wetted with water, the wetted surface is covered with the comminuted and modified cellulose ether, and the web is dried.

It is the object of the present invention to provide a different process that can be carried out with less technical expenditure. In the process according to the present invention, the modified cellulose ether is dispersed in a solution of unmodified cellulose ether in an organic solvent, to which water may be added if necessary, the support is coated on one side or both sides with the dispersion, and is then dried.

The modified cellulose ethers usable in the process may have any form as long as they are comminuted and suspendable. Those cellulose ethers are preferably used which have been modified by cross-linking according to the process described in German Offenlegungsschrift No. 2,357,079, or have been modified according to the process disclosed in German Offenlegungsschrift No. 2,358,150. They have high water absorption and water retention values. Modified cellulose ethers usable within the scope of the invention are also, for example, those disclosed in copending applications Ser. Nos. 683,967, filed May 6, 1976; 683,968, filed May 6, 1976; 682,326, filed May 3, 1976; and 726,000, filed Sept. 23, 1976; in German Pat. No. 839,492 and U.S. Pat. Nos. 3,589,364; 3,723,413; and 2,639,239. These modifications of cellulose ethers lead to products having an acceptable water absorption capacity even if the modified cellulose ether still contains water-soluble parts. Thus in practice cellulose ethers are often not modified to form completely water-insoluble products, and moreover it is not necessary to remove the soluble parts. The soluble portion usually consists of cellulose ether molecules that are either insufficiently modified or not at all.

In a preferred embodiment of the process according to the invention, an alkylhydroxyalkyl cellulose ether is used as an unmodified cellulose ether. The cellulose ether preferably should have a viscosity of about 10 to 30,000 cP in a 2 per cent by weight aqueous solution at 20° C.

Preferably, an alcohol such as methanol, ethanol, propanol-1, propanol-2, butanol-1, butanol-2, methyl propanol-1 or methyl propanol-2, a ketone such as methyl ethyl ketone or diethyl ketone, a chloroderivative of methane such as methylene chloride or chloroform or especially mixtures of these solvents are used as the organic solvent in which the unmodified cellulose ether is dissolved or which is mixed with an aqueous solution of the unmodified cellulose ether at a ratio of 60 to 90 parts by weight to 40 to 10 parts by weight, preferably about 75 to 85 parts by weight to 25 to 15 parts by weight.

For the preparation of the suspension, approximately 1 to 200 g/l, preferably 100 to 160 g/l of comminuted modified cellulose ether having a preferred average particle size of 0.02 to 0.25 mm are added to the solution of organic solvent and the unmodified cellulose ether, to which water may be added if necessary, in such a manner that the suspension to be applied has a viscosity of 20 to 25 seconds, measured in a Ford measuring cup having a 4 mm die.

The hydrophilic web support is composed, for example, of cellulose, wood-pulp, synthetic fibers, especially a polyolefin fiber as described, for example, in German Offenlegungsschrift No. 2,117,370, or of a mixture thereof and has a certain absorption capacity and retention capacity towards liquids. The weight of this material is between 12 and 500 g/m². The supports used for the application of the suspension may or may not be wet strength supports.

The coating of the support with the suspension is carried out in a coating device provided with a roller. The covering of the surface of the support by the layer may be incomplete, for example if the roller in the application device has a screen or punctiform surface structure (e.g. in the case of a gravure printing roll). The quantity of suspension to be applied is determined such that after the coating about 0.5 to 50 g/m² of the modified cellulose ether are on the support.

In addition, a hydrophilic web material having the same composition as, or a composition similar to, the uncoated support may be laminated onto the coated side of the support.

The process according to the invention facilitates the further processing of the absorbent and modified cellulose ethers on carrier materials and thus makes them more easily applicable to a wide range of uses.

The invention will be further illustrated by reference to the following specific examples:

EXAMPLE 1

One side of a cellulose paper having a weight of 24 g/m² is coated in a coating device provided with a roller and having a drying chamber and a suction device for removing solvent vapors. The suspension applied is produced from 200 ml of a 2 per cent by weight aqueous solution of methyl hydroxyethyl cellulose ether having a viscosity of 1,000 cP at 20° C, 800 ml of aqueous isopropanol (87 per cent and 100 g of particles of a carboxymethyl cellulose modified with the cross-linking agent bis-acrylamido acetic acid and having an average particle size of less than 0.2 mm. After drying, more than 10 g/m² of the modified cellulose ether are in the coating. The following example shows one of the purposes for which the coated paper may be used.

EXAMPLE 2

A sample of a size of 100 cm$^2$ is cut out of a coated cellulose paper produced according to Example 1 and is immersed in water for 15 seconds. The water adhering to the surface of the paper after removing the paper from the water is removed by dabbing it with blotting paper, and then the sample is weighed. In its dry state it weighs 0.29 g and in its wet state 1.06 g, which means that is has absorbed 0.77 g of water. A sample of uncoated paper weighs 0.25 g in its dry state and 0.63 g in its wet state, i.e. it has absorbed 0.38 g of water. The absorption capacity of the paper coated according to the invention is thus about twice as high as that of the uncoated paper.

EXAMPLE 3

A tissue paper having a weight of 18 g/m$^2$ is coated as described in Example 1, and the quantity applied is 12.7 g/m$^2$. If samples of this coated paper and of uncoated paper each having a size of 1260 cm$^2$ are dipped into a synthetic urine solution, each of them together with a filter paper sheet having the same size, and after 15 minutes are centrifuged in a laboratory centrifuge at 1000 revolutions per minute, the following figures for the liquid retention value are obtained: the uncoated paper retains 1.1 ml of synthetic urine solution, the coated paper retains 18.5 ml. These figures show a substantially improved retention capacity.

It will be obvious to those skilled in the art that many modifications may be made within the scope of the present invention without departing from the spirit thereof, and the invention includes all such modifications.

What is claimed is:

1. In the process for the transformation of comminuted cellulose ether, which has been rendered at least largely water-insoluble by modification, but which is still highly swellable with water, into an easily workable material, in which process the modified cellulose ether is attached to a hydrophilic support web, the improvement comprising dispersing the modified cellulose ether in a solution of unmodified cellulose ether in an organic solvent, coating the support on at least one of its surfaces with the dispersion and then drying.

2. A process according to claim 1 in which the unmodified cellulose ether is an alkyl hydroxyalky cellulose ether.

3. A process according to claim 1 in which the unmodified cellulose ether has a viscosity of about 10 to 30,000 cP in a 2 per cent by weight aqueous solution at 20° C.

4. A process according to claim 1 including coating the support with approximatey 0.5 to 50 g/m$^2$ of the modified cellulose ether.

5. A process according to claim 1 including using an alcohol, ketone, a chloroderivative of methane or a mixture thereof as an organic solvent.

6. A process according to claim 1 in which the support is not completely coated.

7. A process according to claim 1 in which the coated side of the support is additionally laminated with a hydrophilic material web.

8. A process according to claim 1 in which said organic solvent contains water.

* * * * *